US012629139B2

(12) United States Patent
Forsvall et al.

(10) Patent No.: US 12,629,139 B2
(45) Date of Patent: May 19, 2026

(54) BIOPSY ARRANGEMENTS

(71) Applicant: Xaga Surgical AB, Helsingborg (SE)

(72) Inventors: Andreas Forsvall, Helsingborg (SE);
Krister Uvnäs, Södra Sandby (SE);
Mats Edberg, Eslöv (SE); **Erik
Sparre**, Malmö (SE)

(73) Assignee: Xaga Surgical AB, Helsingborg (SE)

( * ) Notice: Subject to any disclaimer, the term of this
patent is extended or adjusted under 35
U.S.C. 154(b) by 925 days.

(21) Appl. No.: 17/766,032

(22) PCT Filed: Sep. 30, 2020

(86) PCT No.: PCT/EP2020/077367
§ 371 (c)(1),
(2) Date: Apr. 1, 2022

(87) PCT Pub. No.: WO2021/064020
PCT Pub. Date: Apr. 8, 2021

(65) Prior Publication Data
US 2022/0346762 A1    Nov. 3, 2022

(30) Foreign Application Priority Data
Oct. 3, 2019    (EP) .................................... 19201325

(51) Int. Cl.
*A61B 5/00*        (2006.01)
*A61B 10/02*       (2006.01)

(52) U.S. Cl.
CPC .. *A61B 10/0275* (2013.01); *A61B 2010/0208*
(2013.01)

(58) Field of Classification Search
CPC .................... A61B 10/0275; A61B 2010/0208
See application file for complete search history.

(56) References Cited

U.S. PATENT DOCUMENTS

2007/0208272 A1    9/2007    Voegele
2011/0237976 A1    9/2011    Weitzel
(Continued)

FOREIGN PATENT DOCUMENTS

WO    WO03026509      4/2003
WO    WO2007074123    9/2007

OTHER PUBLICATIONS

European Patent Office; International Search Report and Written
Opinion for PCT/EP2020/077367; Nov. 2, 2020; entire document.

*Primary Examiner* — May A Abouelela
(74) *Attorney, Agent, or Firm* — Shore IP Group, PLLC;
Howard J. Klein

(57)    ABSTRACT

An actuator device comprises first, second and third actua-
tors operatively connected to a biopsy needle arrangement
comprising a needle inside a sheath. The needle arrangement
has a closed state and an open state, a tip portion abutting a
needle sheath in the closed state, and the tip portion extend-
ing from the distal end of the needle sheath in the open state.
The first actuator pushes the needle distally in a sliding
direction x relative to the needle sheath a first distance, d1,
at which the needle arrangement is in its open state. The
second actuator pushes the needle sheath distally in the
sliding direction x relative to the needle a second distance,
d2. The third actuator pushes the needle sheath distally in the
sliding direction x relative to the needle a third distance, d3,
where d3 is smaller than d2, at which the needle arrange-
ment is in its closed state.

19 Claims, 5 Drawing Sheets

(56)  References Cited

U.S. PATENT DOCUMENTS

| | | | |
|---|---|---|---|
| 2012/0253230 A1* | 10/2012 | Williams | A61B 10/0275 |
| | | | 600/567 |
| 2015/0088031 A1* | 3/2015 | Paronetto | A61B 10/0233 |
| | | | 600/567 |
| 2015/0150542 A1* | 6/2015 | Robertson | A61B 10/0233 |
| | | | 74/89.39 |
| 2015/0238171 A1* | 8/2015 | Shabaz | A61B 10/0266 |
| | | | 600/567 |
| 2019/0175842 A1* | 6/2019 | Forsvall | A61M 5/3202 |
| 2019/0209144 A1 | 7/2019 | Falkesgaard et al. | |
| 2021/0393243 A1* | 12/2021 | Nevo | A61B 10/0266 |
| 2022/0071607 A1* | 3/2022 | Hvidkjær | A61B 10/0283 |
| 2022/0211356 A1* | 7/2022 | Loh | A61B 10/0266 |
| 2022/0240905 A1* | 8/2022 | Szafran | A61B 17/32056 |
| 2022/0338850 A1* | 10/2022 | Wernersson | A61B 10/0275 |

* cited by examiner

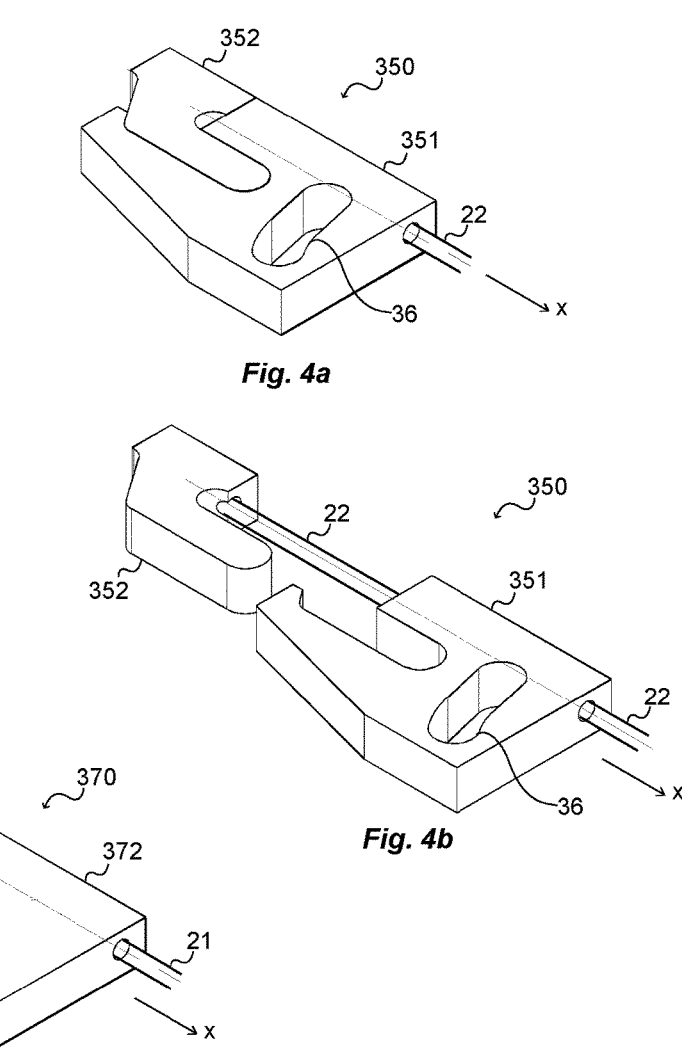
*Fig. 4a*
*Fig. 4b*
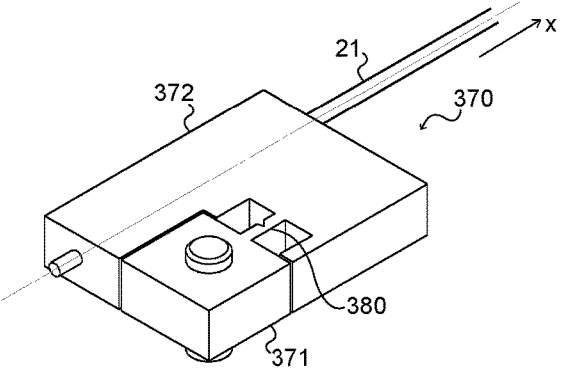
*Fig. 5*
*Fig. 6*
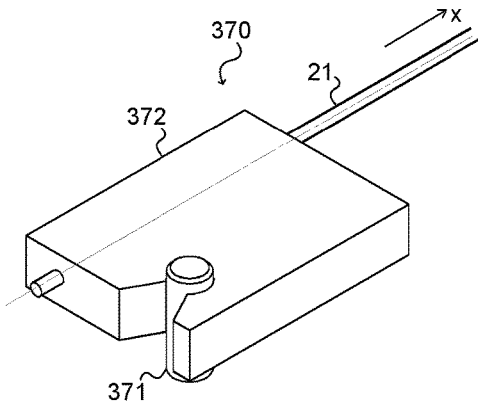
*Fig. 7*

BIOPSY ARRANGEMENTS

CROSS-REFERENCE TO RELATED APPLICATIONS

This application is the § 371 National Stage Entry of International Application No. PCT/EP2020/077367, filed on Sep. 30, 2020, which claims the benefit of European Patent Application No. 19201325.8, filed on Oct. 3, 2019, the contents of which applications are herein incorporated by reference in their entirety.

FIELD OF THE INVENTION

Embodiments herein relate to a biopsy system that comprises an actuator device and a needle arrangement configured to be operatively connected to each other.

BACKGROUND OF THE INVENTION

Within the field of medicine, needle arrangements for various purposes exist, for example needle arrangements for taking biopsy samples. A biopsy sampling arrangement includes, typically, in addition to a needle arrangement also some kind of actuator device that facilitates for an operator to push the biopsy needle into tissue and cut a biopsy sample of tissue. An important issue when performing biopsy sampling is, of course, to safeguard against accidental damage to a patient and to minimize the risks of infection.

Prior art biopsy needles (typically referred as "tru cut" needles") have a drawback in that they collect a large amount of tissue on its way to a target area inside a patient. During insertion, the needle will often encounter areas in which bacteria are present and such bacteria is often transported to areas where they will cause an infection. Such a problem has typically been addressed by the use of antibiotics. However, with the increase of resistance to antibiotics, such a chemical way of addressing the problem has become less efficient and there is a demand for different technical solutions

SUMMARY OF THE INVENTION

In view of the above, and object of the present disclosure is to overcome drawbacks related to prior art biopsy devices.

Such an object is achieved in one aspect by an actuator device for a biopsy needle arrangement. The actuator device comprises a frame, a first actuator, a second actuator and a third actuator. The first, second and third actuators are configured to move in relation to the frame and configured to be operatively connected to the biopsy needle arrangement.

The biopsy needle arrangement comprises a needle sheath and a needle. The needle sheath has a proximal end and a distal end and the needle sheath constitutes an elongated tube having a sheath opening at the distal end of the needle sheath. The needle has a proximal end and a distal end and a length that is greater than the length of the needle sheath. The needle comprises an elongated shaft portion configured to fit inside and slide relative to the needle sheath, and a tip portion connected to the shaft portion and located at the distal end of the needle. The tip portion has a transverse extension, or width, that is greater than a transverse extension, or width, of the sheath opening. The biopsy needle arrangement has a closed state and an open state, the tip portion abutting the needle sheath in the closed state, and the tip portion extending from the distal end of the needle sheath in the open state.

The first actuator is configured to be operatively connected to the needle and configured to, with the needle arrangement in its closed state, push the needle distally in a sliding direction relative to the needle sheath a first distance, $d1$, at which the needle arrangement is in its open state. The second actuator is configured to be operatively connected to the needle sheath and configured to, with the needle arrangement in its open state, push the needle sheath distally in the sliding direction relative to the needle a second distance, $d2$. The third actuator is configured to be operatively connected to the needle sheath and configured to, with the needle arrangement in its open state, push the needle sheath distally in the sliding direction relative to the needle a third distance, $d3$, where $d3$ is smaller than $d2$, at which the needle arrangement is in its closed state. Such a biopsy actuator device differs advantageously from prior art biopsy devices at least in that it is configured to operate in a three-step pushing sequence. The three-step pushing sequence is effective in performing the actual biopsy as well as being safe in terms of minimizing the risk of causing damage to the needle tip portion, and thereby risking injury to a patient. The actuator device configuration makes it possible, following the step of pushing the needle forward into tissue and the step of pushing the sheath forward (thereby cutting a biopsy sample), to avoid an unwanted collision between the sheath and the needle tip. This is due to the fact that the actuator device pushes the sheath forward a relatively long distance when cutting tissue, the length of this second pushing step being just short of the full distance to close the needle arrangement in the closed state. The remaining short distance is then covered by the sheath when actuated by the third actuator during the third step, and thereby closing the needle arrangement.

That is, such an arrangement differs from prior art biopsy systems with tru cut needles. Prior art tru cut needles comprising a needle within a sheath have an open tip. The motion of such a needle is mediated by a prior art actuator in two steps where the needle initially is pushed forward and then the sheath is pushed forward, cutting a tissue sample. There is no need for exact precision in the movement of the sheath since there is no distal stopping arrangement—the prior art sheath moves freely in relation to the needle. Consequently, using a closed tip biopsy needle arrangement as defined herein together with an actuator device according to prior art, a powerful collision would occur between the needle tip and the sheath, resulting in a significant risk of damaging or even dislodging the needle tip from the needle. Needless to say, a damaged or dislodged needle tip inside a patient is an unwanted situation in a biopsy context. Furthermore, a common procedure is to perform multiple biopsies (on one and the same patient) using one and the same needle. In such cases the importance of avoiding damage to the needle is further accentuated because any damage would typically be in the form of edges, lips and cracks that will collect bacteria and thereby increasing the risk of infection.

The mediation of needle and sheath movement in the three steps as obtained by the actuator device described defined herein provides a safe and precise closure of the needle and thereby avoiding the disadvantages of prior art biopsy systems.

The first actuator may be configured to push the needle in motion having a first maximum velocity, the second actuator may be configured to push the needle sheath in motion having a second maximum velocity and the third actuator may be configured to push the needle sheath in motion having a third maximum velocity, where the third maximum velocity is smaller than the second maximum velocity.

Such a configuration of the actuators further accentuates the advantage of minimizing the risk of causing damage to the needle tip portion during the three-step pushing sequence. By minimizing the third velocity, i.e. the velocity of the sheath when setting the needle arrangement into the closed state, any impulse provided by the sheath on the needle tip portion is minimized and the risk of damage is equally minimized.

The actuators may be configured to bias the needle sheath with respect to the tip portion of the needle for all relative positions between the needle sheath and the tip portion.

By biasing the sheath and the tip portion of the needle towards each other, such a configuration of the first and/or second actuator prevents any gap to open between the sheath opening and the tip portion during insertion and retraction of the needle arrangement. For example, such a bias may be achieved by configuring springs in connection with the actuators as will be exemplified below. In other words, the tip portion and the sheath may be biased against each other at all times except when they are in action, i.e. at the time when they are actuated (and at a later point in time when the needle arrangement is opened for removal of a tissue sample). The force by which the tip portion and the sheath are biased against each other is large enough to keep the tip portion of the needle towards the sheath even when the needle arrangement is pushed and pulled through, e.g., tight fasciae.

In other words, a dynamic force is achieved by the configuration described herein due to the fact that the tip portion and the sheath are biased against each other at all times. It is safer than prior art solutions that lock the tip portion and the sheath against each other, using buttons, levers and hatches etc. In such prior art solutions, due to the fact that the needle arrangement in use moves through tissue, the tension between the tip portion and the sheath varies, which may result in an undesired gap between the tip portion and the sheath despite the fact that the parts are locked against each other. In contrast, the configuration described herein overcomes such drawbacks in that a dynamic force is provided, e.g. by the arrangement of springs at the actuators. Moreover, the configuration described herein is simpler than any prior art solution that utilizes a locking mechanism.

The combination of the design of the needle arrangement and the actuator device enables minimization of bacteria translocation and protects the patient against infection while maintaining adequate diagnostics. Remembering that one and the same biopsy needle arrangement may be used to perform multiple biopsies on the same patient, it is important to minimize any bacteria collection on the needle arrangement between the individual biopsies.

Consequently, unwanted collection of, e.g., bacteria on the needle arrangement is minimized during insertion and retraction.

The first actuator may be configured to be releasably attached to the needle via a needle connector, such a needle connector being configured to disengage the needle from the first actuator when the needle is subjected to a force in the sliding direction, which exceeds a threshold force. Also or alternatively, the second actuator may be configured to be releasably attached to the needle sheath via a sheath connector, such a sheath connector being configured to disengage the needle sheath from the second actuator when the needle sheath is subjected to a force in a direction opposite the sliding direction, which exceeds a threshold force.

Such needle and/or sheath connectors may be configured such that they comprise two connector parts, one or both of which is attached to or comprised in respective needle and sheath actuator.

That is, with regard to needle connector parts, the first actuator may be configured to be attached to a first needle connector part of the needle connector, and when the needle disengages from the first actuator, the first needle connector part disengages from a second needle connector part attached to the needle and the second needle connector part moves distally in the sliding direction relative to the first needle connector part. Alternatively, the needle connector may comprise a first needle connector part attached to the first actuator and a second needle connector part configured to be attached to the needle, and when the needle disengages from the first actuator, the first needle connector part disengages from the second needle connector part and the second needle connector part moves distally in the sliding direction relative to the first needle connector part.

Similarly, with regard to sheath connector parts, the second actuator may be configured to be attached to a first sheath connector part of the sheath connector, and when the needle sheath disengages from the second actuator, the first sheath connector part disengages from a second sheath connector part attached to the needle sheath and the first sheath connector part moves distally in the sliding direction relative to the second sheath connector part. Alternatively, the sheath connector may comprise a first sheath connector part attached to the second actuator and a second sheath connector part configured to be attached to the needle sheath, and when the needle sheath disengages from the second actuator, the first sheath connector part disengages from the second sheath connector part and the first sheath connector part moves distally in the sliding direction relative to the second sheath connector part.

Such configurations have the advantageous effects of further preventing the needle arrangement from being damaged as a consequence of an unwanted collision between the sheath and the needle tip during the step of pushing the sheath distally as discussed above. That is, if an unwanted collision between the sheath and the needle tip should occur, the result of which is a force upon the needle tip in the distal direction. In case such a force exceeds a threshold force, which may be determined by the specific configuration of the connector parts as will be discussed in more detail below, the first and second connector parts will separate from each other and the connector part that is attached to the needle and/or the sheath will be disconnected from its respective actuator.

In one aspect there is provided a biopsy needle arrangement that comprises a needle sheath and a needle. The needle sheath has a proximal end and a distal end and the needle sheath constitutes an elongated tube having a sheath opening at the distal end of the needle sheath. The needle has a proximal end and a distal end and a length that is greater than the length of the needle sheath. The needle comprises an elongated shaft portion configured to fit inside and slide relative to the needle sheath and a tip portion connected to the shaft portion and located at the distal end of the needle. The tip portion has a transverse extension, or width, that is greater than a transverse extension, or width, of the sheath opening.

The biopsy needle arrangement is configured to be operatively connected to an actuator device that comprises a first actuator and a second actuator, for example an actuator device as summarized above. The first actuator is configured to be operatively connected to the needle and configured to push the needle distally in a sliding direction relative to the needle sheath. The second actuator is configured to be operatively connected to the needle sheath and configured to push the needle sheath distally in the sliding direction relative to the needle.

The biopsy needle arrangement further comprises a needle connector configured to attach the needle to the first actuator, and a sheath connector configured to attach the needle sheath to the second actuator.

The needle connector is configured to disengage the needle from the first actuator when the needle is subjected to a force in the sliding direction, which exceeds a threshold force. Also or alternatively, the sheath connector is configured to disengage the needle sheath from the second actuator when the needle sheath is subjected to a force in a direction opposite the sliding direction, which exceeds a threshold force.

Such a configuration has the advantageous effects of preventing the needle arrangement from being damaged as a consequence of an unwanted collision between the sheath and the needle tip during the step of pushing the sheath distally as discussed above.

The sheath connector may comprise a groove that is aligned along at least a first transverse direction relative to the sliding direction. Such a groove is configured to cooperate with a pin of a third actuator of the actuator device, the pin being configured to slide relative to the second actuator in a second transverse direction relative to the sliding direction, the second transverse direction being at an angle a to the first transverse direction.

Such a configuration further improves the advantage of preventing the needle arrangement from being damaged as a consequence of an unwanted collision between the sheath and the needle tip during the step of pushing the sheath distally as discussed above.

The needle connector may comprise a first needle connector part configured to be attached to the first actuator, and a second needle connector part attached to the needle, and when the needle disengages from the first actuator, the first needle connector part disengages from the second needle connector part and the second needle connector part moves distally in the sliding direction relative to the first needle connector part.

Similarly, the sheath connector may comprise a first sheath connector part configured to be attached to the second actuator, and a second sheath connector part attached to the needle sheath, and when the needle sheath disengages from the second actuator, the first sheath connector part disengages from the second sheath connector part and the first sheath connector part moves distally in the sliding direction relative to the second sheath connector part.

Such configurations further accentuate the advantageous effects of preventing the needle arrangement from being damaged as a consequence of an unwanted collision between the sheath and the needle tip during the step of pushing the sheath distally as discussed above. That is, if an unwanted collision between the sheath and the needle tip should occur, the result of which is a force upon the needle tip in the distal direction. In case such a force exceeds a threshold force, which may be determined by the specific configuration of the connector parts as will be discussed in more detail below, the first and second connector parts will separate from each other and the connector part that is attached to the needle and/or the sheath will be prevented from moving further in the distal direction.

In one aspect there is provided biopsy system comprising an actuator device and a biopsy needle arrangement as summarized above. Such a system may be considered as a disposable arrangement. Effects and advantages of such a system correspond to those summarized above in relation to the various configurations of the actuator and the biopsy needle arrangement.

BRIEF DESCRIPTION OF THE DRAWINGS

FIGS. 4a-b are schematically illustrated views of a two-part click-fit connector.

FIG. 5 is a schematically illustrated view of a two-part click-fit connector.

FIG. 6 is a schematically illustrated view of a two-part break-apart connector.

FIG. 7 is a schematically illustrated view of a two-part friction-fit connector.

DETAILED DESCRIPTION OF PREFERRED EMBODIMENT

Figures 1, 2:
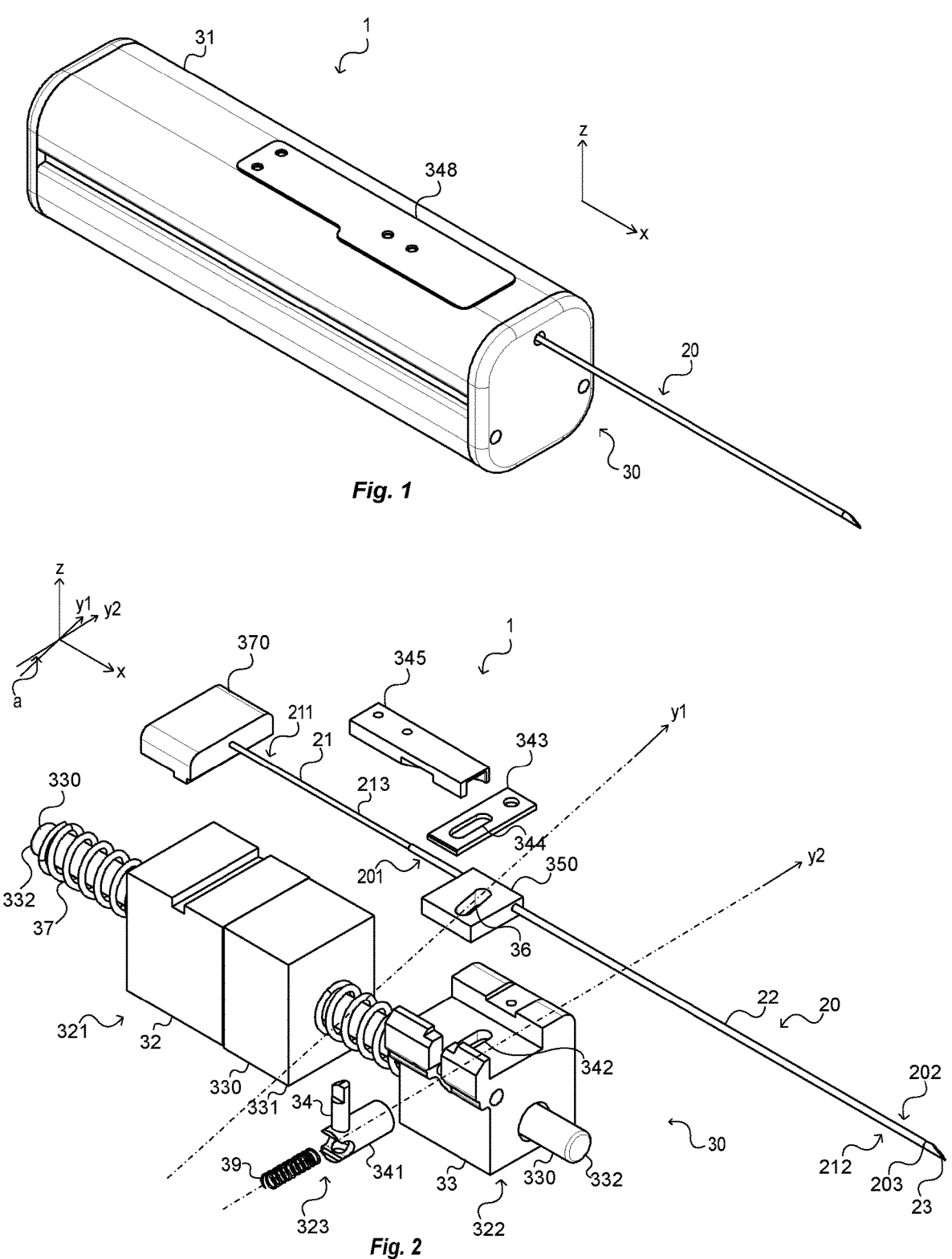
FIG. 1 is a schematically illustrated perspective view of a biopsy system.
FIG. 2 is a schematically illustrated exploded view of a biopsy system comprising an actuator device and a needle arrangement.

FIGS. 1 and 2 illustrate a biopsy system 1 comprising an actuator device 30 and a biopsy needle arrangement 20. The actuator device 30 comprises a frame 330, a first actuator 321, a second actuator 322 and a third actuator 323. The first, second and third actuators 321, 322, 323 are configured to move in relation to the frame 330 and configured to be operatively connected to the biopsy needle arrangement 20.

The biopsy needle arrangement 20 comprises a needle sheath 22 and a needle 21. The needle sheath 22 has a proximal end 201 and a distal end 202 and the needle sheath 22 constitutes an elongated tube that has a sheath opening 203 at the distal end 202 of the needle sheath 22. The needle 21 has a proximal end 211 and a distal end 212 and a length that is greater than the length of the needle sheath 22. The needle 21 comprises an elongated shaft portion 213 configured to fit inside and slide relative to the needle sheath 22, and a tip portion 23 connected to the shaft portion 213. The tip portion 23 is located at the distal end 212 of the needle 21 and the tip portion 23 has a transverse extension, or width, that is greater than a transverse extension, or width, of the sheath opening 203. The transverse extension, or width, of the tip portion 23 may advantageously be equal to the outer transverse extension, or width, of the sheath 22 and thereby making the outer surface smooth and thus minimizing the risk of collecting bacteria during use, as discussed above. Furthermore, although the illustrated sheath opening 203 and the tip portion 23 define an abutting plane that is perpendicular to the direction x that defines the extension of the needle arrangement 20, other geometries may be configured. For example, the sheath opening 203 and the tip portion 23 may define an abutting plane that is at an angle to the direction x that is not a right angle, for example an angle in the interval 20-90 degrees.

For further exemplifying details regarding the needle arrangement 20, reference is made to European patent application 17700660 by the same applicant. For example, the needle arrangement may be subject of surface treatment and heat coating for the purpose of minimizing transfer of bacteria.

Figures 3A, 3B:
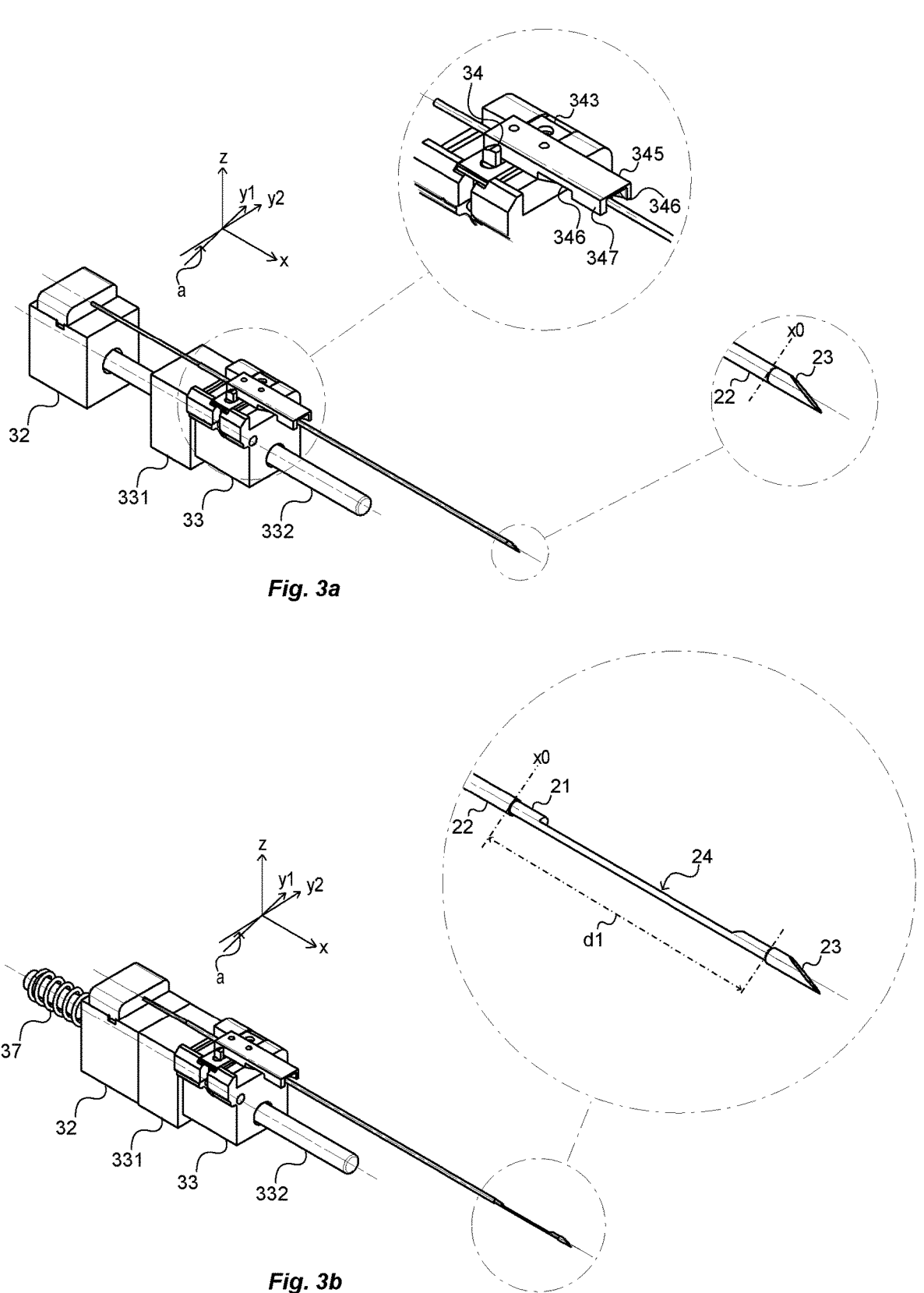
FIGS. 3a-3d are schematically illustrated views of a three-step pushing sequence performed by of a biopsy system comprising an actuator device and a needle arrangement.

Now with reference also to FIGS. 3*a-d*, the biopsy needle arrangement 20 has a closed state and an open state, the tip portion 23 abutting the needle sheath 22 in the closed state as shown in FIG. 3*a*, where x0 defines an origin in the sliding direction x in the closed state. The tip portion 23 extends from the distal end 202 of the needle sheath 22 in the open state as shown in FIG. 3*b*.

The first actuator 321 is configured to be operatively connected to the needle 21 and configured to, with the needle arrangement 20 in its closed state, push the needle 21, from the origin x0, distally in a sliding direction x relative to the needle sheath 22 a first distance, d1, at which the needle arrangement 20 is in its open state. That is, a first pushing step of a three-step pushing sequence is exemplified by the transition from the closed state shown in FIG. 3*a* to the open state shown FIG. 3*b*. During such a first pushing step, the needle will enter into tissue and a hollow 24 at the proximal end of the needle 21 will be filled with the tissue that is the subject of biopsy sampling.

The second actuator 322 is configured to be operatively connected to the needle sheath 22 and configured to, with the needle arrangement 20 in its open state, push the needle sheath 22 distally in the sliding direction x relative to the needle 21 a second distance, d2. That is, a second pushing step of the three-step pushing sequence is exemplified by the transition from the open state shown in FIG. 3*b* to the open state shown FIG. 3*c* (remembering that the open state remains as long as the tip portion 23 of the needle 21 is not abutting the needle sheath 22). During such a second pushing step, the needle sheath 22 will cut a tissue sample that will be held in the hollow 24 in the needle 21.

Such connections of the first actuator 321 with the needle 21 and the second actuator 322 with the sheath 22 may be realized as exemplified in FIG. 2 by means of a needle connector 370 and a sheath connector 350, respectively.

By configuring the needle connector 370 and the sheath connector 350, for example by configuring their respective attachment to the first and second actuators 321, 322 in terms of elasticity, it is possible to obtain a configuration of the first actuator 321 and/or the second actuator 322 to spring bias the needle sheath 22 with respect to the tip portion 23 of the needle 21 for all relative positions between the needle sheath 22 and the tip portion 23.

The third actuator 323 is configured to be operatively connected to the needle sheath 22 and configured to, with the needle arrangement in its open state, push the needle sheath 22 distally in the sliding direction x relative to the needle 21 a third distance, d3, where d3 is smaller than d2, at which the needle arrangement 20 is in its closed state. That is, a third pushing step of the three-step pushing sequence is exemplified by the transition from the open state shown in FIG. 3*c* to the closed state shown FIG. 3*d*.

With regard to the three-step pushing sequence, the first actuator 321 may be configured to push the needle 21 in motion having a first maximum velocity, v1. The second actuator 322 may be configured to push the needle sheath 22 in motion having a second maximum velocity, v2. The third actuator 323 may be configured to push the needle sheath 22 in motion having a third maximum velocity, v3, where v3 is smaller than v2.

As exemplified in FIGS. 1 to 3, the first actuator 321 may comprise a first slider 32 and a spring 37. The first slider is in such an example configured to slide relative to the frame 330 in the sliding direction x and the first spring 37 is configured to bias the first slider 32 relative to the frame 330. Similarly, the second actuator 322 may comprise a second slider 33 and a second spring 38. The second slider 33 is then configured to slide relative to the frame 330 in the sliding direction x and the second spring 38 is configured to bias the second slider 33 relative to the frame 330. The third actuator 323 may comprise a pin 34 and a third spring 39. The third spring 39 is then configured to bias the pin 34 relative to the second slider 33.

Such a configuration of the actuators provides a dynamic force that keeps the tip portion 23 and the sheath 22 biased against each other when the needle arrangement 20 is inserted and retracted through tissue, the advantages of which have been summarized above.

As exemplified, the frame 330 may comprise a frame base 331 and an axle 332, the axle 332 having a longitudinal extension in the sliding direction x and being arranged through the frame base 331. The first and second actuators 321, 322 are in such an example arranged along the axle 332 on a respective proximal and distal side of the frame base 331 and the respective springs 37, 38 are arranged to provide forces for pushing the first and second actuators 321, 322 as discussed above.

The configurations of the first and second actuators 321, 322 to push the needle 21 and the sheath 22 distally in the sliding direction x the first and second distances d1 and d2 may involve configuration of the respective sliders 32, 33 in terms of their respective size and position in relation to the parts 331, 332 of the frame 330. With regard to the configuration of the actuators 321, 322 in terms of pushing the needle 21 and sheath 22 in motion with the velocities v1 and v2, respectively, the respective springs 37, 38 may be chosen in terms of length and other characteristics to provide appropriate forces.

With regard to the third actuator 323, the pin 34 may be configured to cooperate with a groove 36 in the sheath connector 350 attached to the needle sheath 22. As exemplified, the groove 36 may be aligned along at least a first transverse direction y1 relative to the sliding direction x and the pin 34 may be configured to slide relative to the second actuator 322 in a second transverse direction y2 relative to the sliding direction x. The second transverse direction y2 is at an angle a to the first transverse direction y1. Although FIGS. 2 and 3*a-d* exemplify the groove 36 as being straight along the first direction y1, it will be exemplified below that the groove 36 may be curved and thereby being defined by a continuum of directions, including the first transverse direction y1, that differ from the second transverse direction y2. Furthermore, as exemplified in FIGS. 2 and 3*a-d*, the pin 34 may be attached to a pin base 341 cooperate with a groove 342 in the second actuator 322 and with a groove 344 in a first pin guider 343 in order to be guided, when pushed by the third spring 39 arranged inside the pin base 341, along the second transverse direction y2. The pin guider 343 may be arranged, as exemplified in the drawings on top of (i.e. as defined by the z direction) the sheath connector 350 or, e.g, between the sheath connector 350 and the second actuator 322.

By configuring the groove 36 in the sheath connector 350 with a first transverse direction y1 (or with a curve defined by a continuum of directions, including the first transverse direction y1) in relation to the second transverse direction y2 it is possible to configure the third distance d3 and the third velocity v3 (or varying velocity v3 in case the groove 36 is curved) with which the needle sheath 22 is pushed during the third pushing step of the three-step pushing sequence described above takes place. It is to be noted that the third spring 39 may be configured in terms of length and other characteristics to push the pin 34 along the grooves 342, 344 with an appropriate velocity.

As indicated in FIG. 3a, the first, second and third actuators 321, 322, 323 are loaded with potential energy by the respective springs 37, 38, 39 being compressed along their respective configured directions x and y2. That is, the first actuator 321 is loaded by retraction of the first slider 32 in the direction –x, opposite the sliding direction x, to a proximal position in relation to the axle 332 of the frame 330. The retraction may take place by way of manual interaction with the first slider 32, directly or via any appropriate assisting retraction arrangement, and locked in the retracted position by appropriate locking means, the details of which are outside the scope of the present disclosure.

Similarly, the second actuator 322 is loaded by retraction of the second slider 33 in the direction –x, opposite the sliding direction x, to a position immediately distal in relation to the frame base 331 of the frame 330. Having been retracted, the positions of the first and second sliders 22, 23 in relation to the frame base 331 establishes the x0 origin in the closed state and a constant closing force is provided by the tip portion 23 on the sheath 22. As for the first actuator 321, the retraction of the second slider 33 may take place by way of manual interaction with the second slider 33, directly or via any appropriate assisting retraction arrangement, and locked in the retracted position by appropriate locking means, the details of which are outside the scope of the present disclosure.

Figures 3C, 3D:
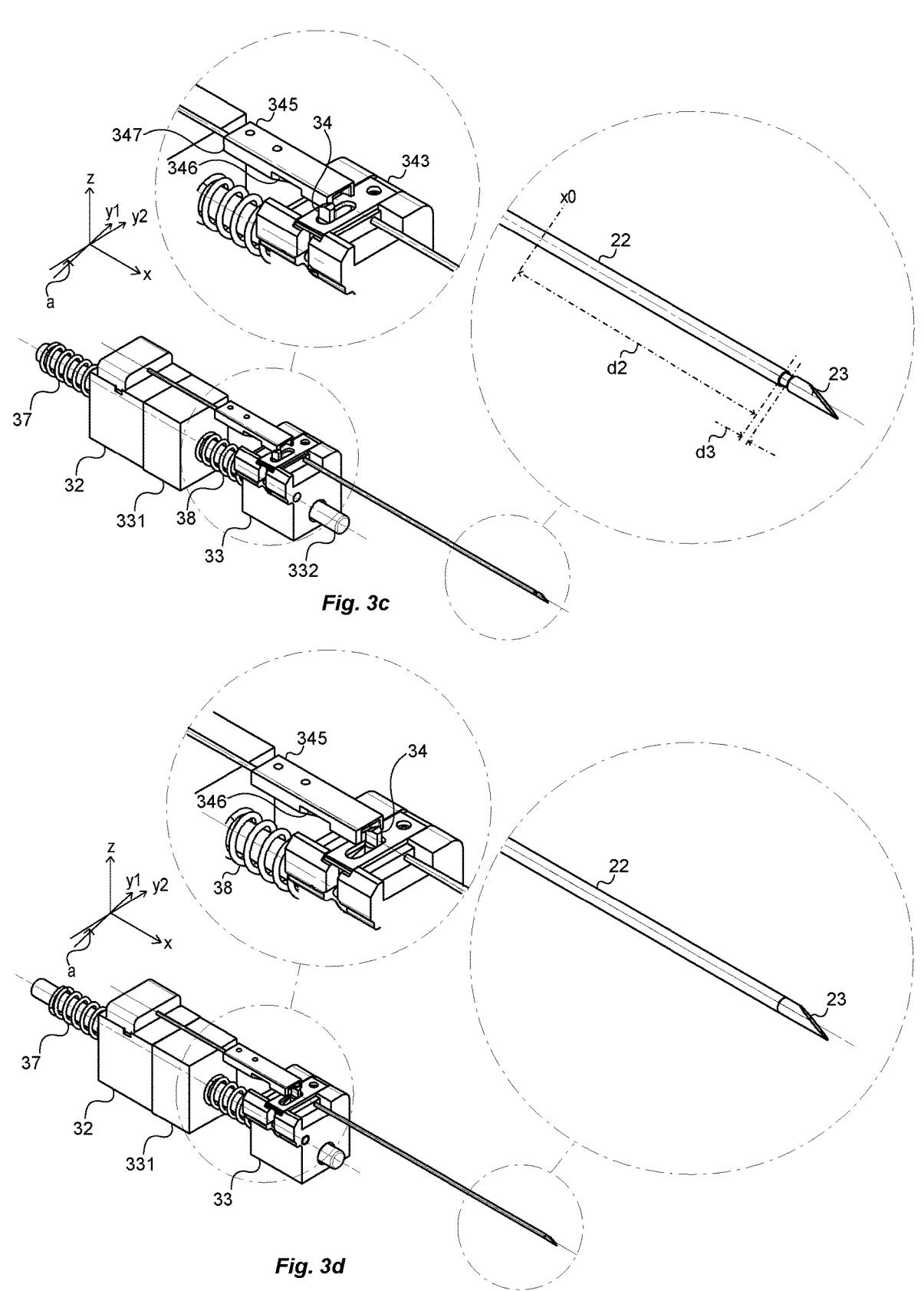

The third actuator 323 is loaded as a consequence of the retraction of the second slider 33 as described above and as a consequence of interaction with a second pin guider 345. Starting from an unloaded state as illustrated in FIG. 3d, where the pin 34 is at a position along the direction y2 that places the pin 34 immediately distal in relation to the second pin guider 345. The second pin guider 345 is configured with a guiding groove 346 that guides the pin 34, when retracted in the direction –x by the retraction of the second slider 33, in the direction –y2, opposite the second transverse direction y2, to a position in relation to the second pin guider 345 as illustrated in FIG. 3a.

As exemplified, the guiding groove 346 runs from the distal end of the second pin guider 345 and exits a side portion 347 in the second pin guider 345. The second pin guider 345 is resilient in a direction z, the resilience being obtained by being attached to a leaf spring 348 that is fixed to, or being a part of, the housing 31. When being retracted along the –x direction inside the guiding groove 346, the pin 34 forces the second pin guider 345 to flex in the direction z due to its resilience. When exiting the side portion 347 of the second pin guider 345, the second pin guider 345 flexes back opposite the –z direction. Due to the fact that the side portion opening 347 has a limited extent in the direction z, the pin 34 will be able to, when being pushed distally in the sliding direction x during the third pushing step of the three-step pushing sequence, avoid being guided back into the guiding groove 346. This avoidance of being guided back into the guiding groove 346 can be inferred from the position of the pin 34 shown in FIGS. 3a and 3c.

Having been loaded with potential energy by the respective springs 37, 38, 39 as described above, the first, second and third actuators 321, 322, 323 may be triggered to release their potential energy by a triggering assembly. Such a triggering assembly performs the function of, for example as a consequence of a manual interaction, releasing the first actuator 321, which in turn releases the second actuator 322 and the third actuator 323, resulting in the three-step pushing sequence as described above.

Advantageously, the triggering of the third actuator 323 should not take place until the second actuator 322 has stopped moving in the sliding direction x, which may be achieved by configuring the pin 34 and the second pin guider 345 such that they fit tightly with respect to each other. Further details regarding a triggering assembly will be exemplified below in connection with FIG. 8a.

Having been triggered, the needle arrangement 20 is subjected to the three-step sequence as described, following which the closed state is reached and a constant closing force is provided by the top portion 23 on the sheath 22. This closing force by the tip 23 on the sheath 22 is in this closed state provided by the force of the third spring 39 via the pin 34 actng on the sheath connector 35 via the grove 36.

As summarized above, an advantage of the arrangements described herein, is that various configurations of the actuator device 30 and the needle arrangement 20 enable prevention of the needle arrangement 20 from being damaged as a consequence of an unwanted collision between the needle sheath 22 and the needle tip portion 23 during the step of pushing the sheath 22 distally.

For example, the first actuator 321 may be configured to be releasably attached to the needle 21 via the needle connector 370, the needle connector 370 being configured to disengage the needle 21 from the first actuator 321 when the needle 21 is subjected to a force in the sliding direction x, which exceeds a threshold force. Also or alternatively, the second actuator 322 may be configured to be releasably attached to the needle sheath 22 via the sheath connector 350, the sheath connector 350 being configured to disengage the needle sheath 22 from the second actuator 322 when the needle sheath 22 is subjected to a force in a direction –x opposite the sliding direction x, which exceeds a threshold force. Such force limiting security configurations of the actuator device 30 and the needle arrangement 20 may be realized in various ways as will be exemplified in the following and with reference to FIGS. 4a-b and FIGS. 5 to 7.

For example, the first actuator 321 may be configured to be attached to a first needle connector part 371 of the needle connector 370. For such a configuration, when the needle 21 disengages from the first actuator 321, the first needle connector part 371 disengages from a second needle connector part 372 attached to the needle 21 and the second needle connector part 372 moves distally in the sliding direction x relative to the first needle connector part 371.

Alternatively, the needle connector 370 may comprise a first needle connector part 371 attached to the first actuator 321 and a second needle connector part 372 configured to be attached to the needle 21. For such a configuration, when the needle 21 disengages from the first actuator 321, the first needle connector part 371 disengages from the second needle connector part 372 and the second needle connector part 372 moves distally in the sliding direction x relative to the first needle connector part 371.

Similarly, the second actuator 322 may be configured to be attached to a first sheath connector part 351 of the sheath connector 350. For such a configuration, when the needle sheath 22 disengages from the second actuator 322, the first sheath connector part 351 disengages from a second sheath connector part 352 attached to the needle sheath 22 and the first sheath connector part 351 moves distally in the sliding direction x relative to the second sheath connector part 352.

Alternatively, the sheath connector 350 may comprise a first sheath connector part 351 attached to the second actuator 322 and a second sheath connector part 352 configured to be attached to the needle sheath 22. For such a configuration, when the needle sheath 22 disengages from the second actuator 322, the first sheath connector part 351 disengages from the second sheath connector part 352 and the first sheath connector part 351 moves distally in the sliding direction x relative to the second sheath connector part 352.

The needle connector 370 and/or the sheath connector 350 may be in the form of a click-fit configuration of the respective first and second connector parts 371, 372, 351, 352.

FIG. 4a exemplifies such a click-fit sheath connector 350 with the first sheath connector part 351 configured to be attached to the second actuator 322 and a second connector part 352 attached to the sheath 22. The first connector part 351 is configured to move freely with respect to the sheath 22. The first connector part 351 interacts with the pin 34 of the third actuator 323 via the groove 36 (here exemplified by a curved groove 36). Configuration of the threshold force at which the click-fit disengages, as illustrated in FIG. 4b, may be realized by an appropriate selection of the material of the connector 350 and the spatial dimensions of the first and second connector parts 351, 352, as the skilled person will realize.

FIG. 5 exemplifies such a click-fit needle connector 370 with the first needle connector part 371 configured to be attached to the first actuator 321 and a second connector part 372 attached to the needle 21. Configuration of the threshold force at which the click-fit disengages may be realized by an appropriate selection of the material of the connector 370 and the spatial dimensions of the first and second connector parts 371, 372, as the skilled person will realize.

The needle connector 370 and/or the sheath connector 350 may be in the form of a break-apart configuration of the respective first and second connector parts 371, 372, 351, 352.

FIG. 6 exemplifies such a break-apart needle connector 370 with the first connector part 371 configured to be attached to the first actuator 321 and a second connector part 372 configured to be attached to the needle 21. When the needle 21 is subjected to a force in the sliding direction x which exceeds a threshold force, a connector bridge 380 breaks and the second connector part 372 moves distally in the sliding direction x relative to the first connector part 371. Configuration of the threshold force at which the connector bridge 380 breaks may be realized by selection of the material of the connector 370 (including the connector bridge 380) and the spatial dimensions of the connector bridge 380, as the skilled person will realize.

The needle connector 370 and/or the sheath connector 350 may be in the form of a friction fit configuration of the respective first and second connector parts 371, 372, 351, 352.

FIG. 7 exemplifies such a friction-fit needle connector 370 with the first connector part 371 configured to be attached to the first actuator 321 and a second connector part 372 configured to be attached to the needle 21. When the needle 21 is subjected to a force in the sliding direction x which exceeds a threshold force, friction forces between the first and second connector parts 371, 372 at are overcome by the force in the sliding direction x, and the second connector part 372 moves distally in the sliding direction x relative to the first connector part 371. Configuration of the threshold force at which the friction forces are overcome may be realized by selection of the material of the connector 370 and the spatial dimensions of the friction fit between the connector parts 371, 372, as the skilled person will realize.

In the embodiments exemplified above, the third actuator 323 is configured to be operatively connected to the needle sheath 22 and configured to, with the needle arrangement 20 in its open state, push the needle sheath 23 distally in the sliding direction x relative to the needle 21 a third distance, d3, where d3 is smaller than d2, at which the needle arrangement 20 is in its closed state. That is, in general terms, a three-step sequence is performed to open and then close the needle arrangement 20 wherein the third step comprises a short relative movement between the needle 21 and the sheath 22. Examples of such a three-step sequence have been described that comprise three pushing steps.

However, it is foreseen that such a three-step sequence may involve both pushing and pulling steps. That is, in other examples a third actuator may be configured to, subsequent to the pushing of the needle and the sheath distally, pull the needle backwards in the proximal direction a small distance and at a limited speed. Such a configuration may be realized by an arrangement of the third actuator at the first actuator. In such examples, a needle connector may have a groove along a direction that is aligned along a direction that is +/−180 degrees in relation to the groove 36 exemplified above in connection with the description of the third actuator 323.

In the above, focus has been on describing the actuator device 30 and its various exemplifying configurations for interaction with the biopsy needle arrangement 20. In the following, focus will be made on describing the biopsy needle arrangement 20 and various exemplifying configurations for interaction with the actuator device 30. Reference is made to FIGS. 1 to 7.

Such a biopsy needle arrangement 20 comprises a needle sheath 22 that has proximal end 201 and a distal end 202. The needle sheath 22 constitutes an elongated tube having a sheath opening 203 at the distal end 202 of the needle sheath 22.

The biopsy needle arrangement 20 further comprises a needle 21 that has proximal end 211 and a distal end 212 and a length that is greater than the length of the needle sheath 22. The needle 21 comprises an elongated shaft portion 213 configured to fit inside and slide relative to the needle sheath 22, and a tip portion 23 connected to the shaft portion 213 and located at the distal end 212 of the needle 21. The tip portion 23 has a transverse extension, or width, that is greater than a transverse extension, or width, of the sheath opening 203. The transverse extension, or width, of the tip portion 23 may advantageously be equal to the outer transverse extension, or width, of the sheath 22 and thereby minimizing the risk of collecting bacteria during use, as discussed above. Furthermore, although the illustrated sheath opening 203 and the tip portion 23 define an abutting plane that is perpendicular to the direction x that defines the extension of the needle arrangement 20, other geometries may be configured. For example, the sheath opening 203 and the tip portion 23 may define an abutting plane that is at an angle to the direction x that is not a right angle, for example an angle in the interval 20-90 degrees.

The biopsy needle arrangement 20 is configured to be operatively connected to an actuator device 30 that comprises a first actuator 321 and a second actuator 322, the first actuator 321 being configured to be operatively connected to the needle 21 and configured to push the needle 21 distally in a sliding direction x relative to the needle sheath 22 and the second actuator 322 being configured to be operatively connected to the needle sheath 22 and configured to push the needle sheath 22 distally in the sliding direction x relative to the needle 21.

The biopsy needle arrangement 20 further comprises a needle connector 370 configured to attach the needle 21 to the first actuator 321, and a sheath connector 350 configured to attach the needle sheath 22 to the second actuator 322. The needle connector 370 is configured to disengage the needle 21 from the first actuator 321 when the needle 21 is subjected to a force in the sliding direction x, which exceeds a threshold force. Also or alternatively, the sheath connector 350 is configured to disengage the needle sheath 22 from the second actuator 322 when the needle sheath 22 is subjected to a force in a direction –x opposite the sliding direction x, which exceeds a threshold force.

The sheath connector 350 may comprise a groove 36 aligned along at least a first transverse direction y1 relative to the sliding direction x, the groove 36 being configured to cooperate with a pin 34 of a third actuator 323 of the actuator device 30. Such a pin 34 is configured to slide relative to the second actuator 322 in a second transverse direction y2 relative to the sliding direction x, the second transverse direction y2 being at an angle a to the first transverse direction y1. The groove 36 may be curved in a continuum of directions, including the first transverse direction y1.

The needle connector 370 may comprise a first needle connector part 371 configured to be attached to the first actuator 321, and a second needle connector part 372 attached to the needle 21. For such a configuration, when the needle 21 disengages from the first actuator 321, the first needle connector part 371 disengages from the second needle connector part 372 and the second needle connector part 372 moves distally in the sliding direction x relative to the first needle connector part 371.

The sheath connector 350 may comprise a first sheath connector part 351 configured to be attached to the second actuator 322, and a second sheath connector part 352 attached to the needle sheath 22. For such a configuration, when the needle sheath 22 disengages from the second actuator 322, the first sheath connector part 351 disengages from the second sheath connector part 352 and the first sheath connector part 351 moves distally in the sliding direction x relative to the second sheath connector part 352.

The needle connector 370 and/or the sheath connector 350 may be a click-fit configuration of the respective first and second connector parts 371, 372, 351, 352. The needle connector 370 and/or the sheath connector 350 may be a break-apart configuration of the respective first and second connector parts 371, 372, 351, 352. The needle connector 370 and/or the sheath connector 350 may be a friction fit configuration of the respective first and second connector parts 371, 372, 351, 352.

As mentioned above, a combination of an actuator device 30 and a needle arrangement 20 is one example of a biopsy system 1 where the system 1 may be considered as a disposable device for use with the (non-disposable) actuator device 30. However, although not explicitly illustrated, other combinations of parts may define other systems. For example, a biopsy system may be defined as a combination of the needle arrangement 20 together with at least parts of the first and second sliders 32, 33 that are configured to be connected to the actuator device 30. Such a system may be considered as a disposable device for use with the (non-disposable) actuator device.

Finally, with reference to FIGS. 1 to 7, a biopsy needle arrangement 20 may comprise:

a needle sheath 22 having proximal end 201 and a distal end 202, the needle sheath 22 constituting an elongated tube having a sheath opening 203 at the distal end 202 of the needle sheath 22.

a needle 21 having proximal end 211 and a distal end 212 and a length that is greater than the length of the needle sheath 22, the needle 21 comprising an elongated shaft portion 213 configured to fit inside and slide relative to the needle sheath 22, and a tip portion 23 connected to the shaft portion 213 and located at the distal end 212 of the needle 21, the tip portion 23 having a transverse extension, or width, that is greater than a transverse extension, or width, of the sheath opening 203, wherein:

the biopsy needle arrangement 20 is configured to be operatively connected to an actuator device 30 that comprises a first actuator 321 and a second actuator 322, the first actuator 321 being configured to be operatively connected to the needle 21 and configured to push the needle 21 distally in a sliding direction x relative to the needle sheath 22 and the second actuator 322 being configured to be operatively connected to the needle sheath 22 and configured to push the needle sheath 22 distally in the sliding direction x relative to the needle 21, wherein the biopsy needle arrangement 20 further comprises:

a needle connector 370 configured to attach the needle 21 to the first actuator 321, and a sheath connector 350 configured to attach the needle sheath 22 to the second actuator 322, wherein:

the needle connector 370 is configured to disengage the needle 21 from the first actuator 321 when the needle 21 is subjected to a force in the sliding direction x, which exceeds a threshold force, and/or the sheath connector 350 is configured to disengage the needle sheath 22 from the second actuator 322 when the needle sheath 22 is subjected to a force in a direction –x opposite the sliding direction x, which exceeds a threshold force.

For example:

the sheath connector 350 comprises a groove 36 aligned along at least a first transverse direction y1 relative to the sliding direction x, the groove 36 being configured to cooperate with a pin 34 of a third actuator 323 of the actuator device 30, the pin 34 being configured to slide relative to the second actuator 322 in a second transverse direction y2 relative to the sliding direction x, the second transverse direction y2 being at an angle a to the first transverse direction y1.

For example:

the groove 36 is curved in a continuum of directions, including the first transverse direction y1.

For example:

the needle connector 370 comprises a first needle connector part 371 configured to be attached to the first actuator 321, and a second needle connector part 372 attached to the needle 21, and when the needle 21 disengages from the first actuator 321, the first needle connector part 371 disengages from the second needle connector part 372 and the second needle connector part 372 moves distally in the sliding direction x relative to the first needle connector part 371.

For example:

the sheath connector 350 comprises a first sheath connector part 351 configured to be attached to the second actuator 322, and a second sheath connector part 352 attached to the needle sheath 22, and when the needle sheath 22 disengages from the second actuator 322, the first sheath connector part 351 disengages from the second sheath connector part 352 and the first sheath connector part 351 moves distally in the sliding direction x relative to the second sheath connector part 352.

For example:

the needle connector 370 and/or the sheath connector 350 is a click-fit configuration of the respective first and second connector parts 371, 372, 351, 352.

For example:

the needle connector 370 and/or the sheath connector 350 is a break-apart configuration of the respective first and second connector parts 371, 372, 351, 352.

For example:

the needle connector 370 and/or the sheath connector 350 is a friction fit configuration of the respective first and second connector parts 371, 372, 351, 352.

Figure 8A:
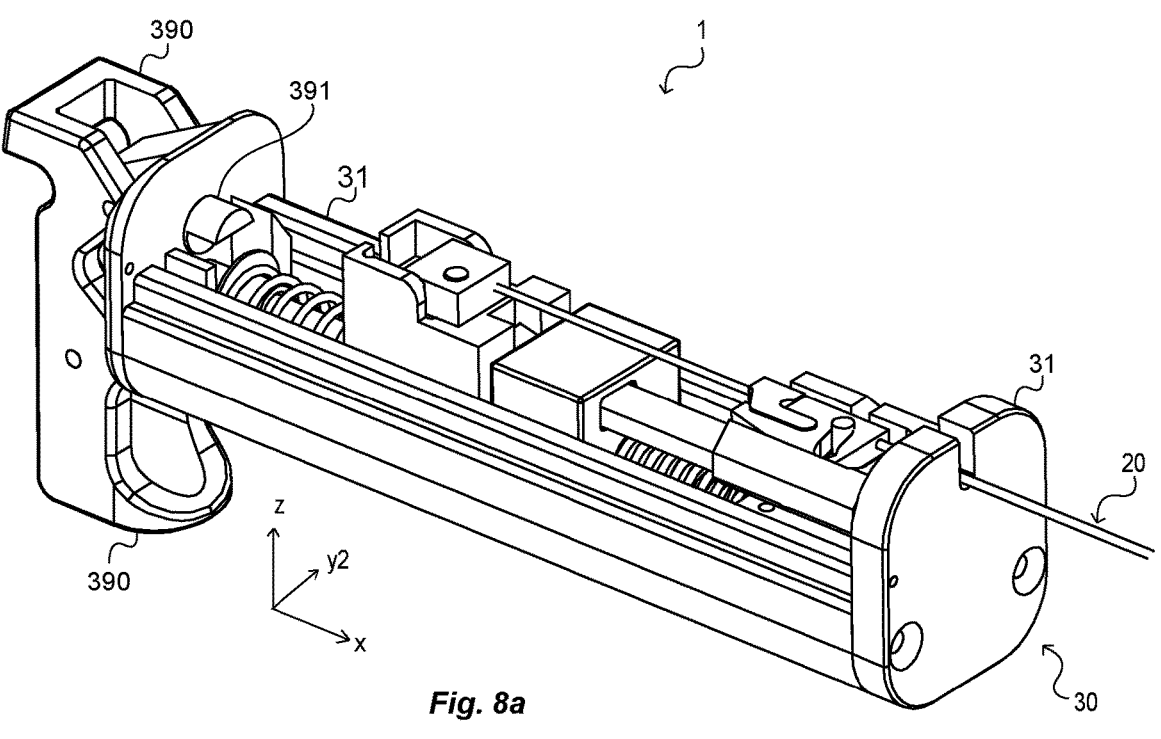
FIG. 8a is a schematically illustrated perspective view of a biopsy system.
Figure 8B:
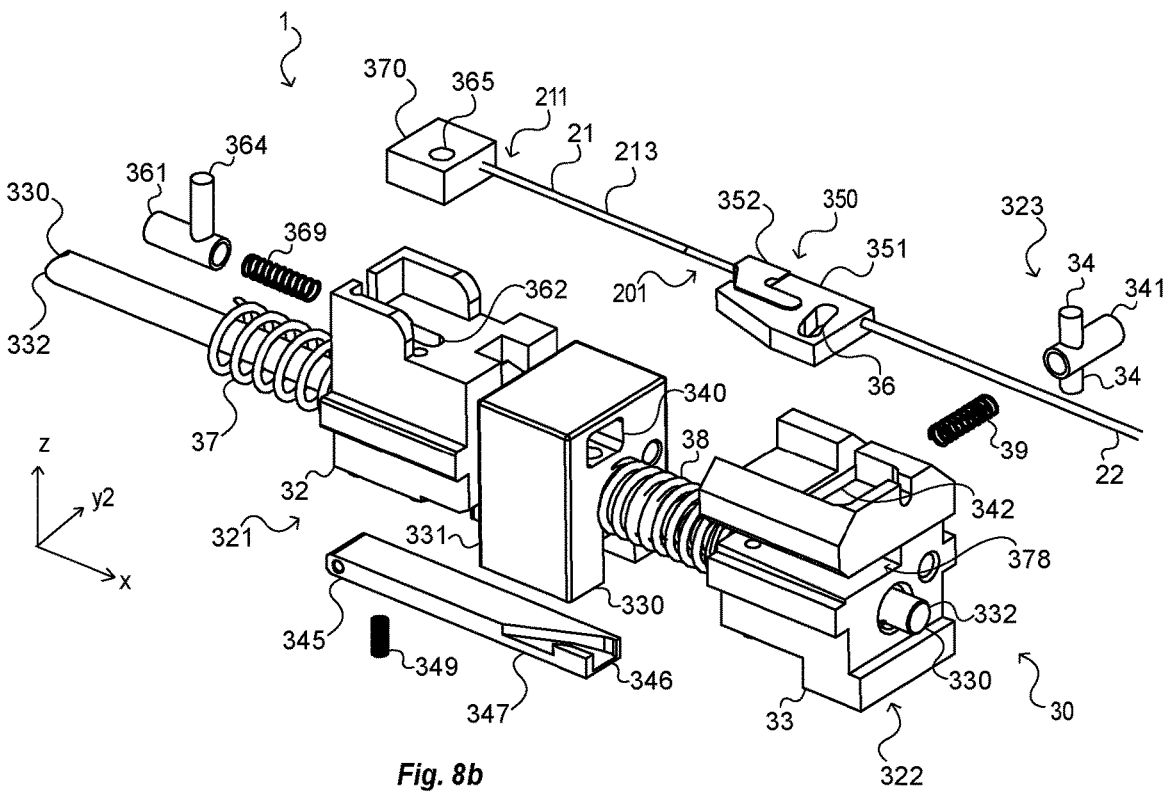
FIG. 8b is a schematically illustrated exploded view of a biopsy system.

Turning now to FIG. 8a and FIG. 8b, further embodiments of a biopsy system 1 comprising an actuator device 30 and a biopsy needle arrangement 20 will be described. The actuator device 30 comprises a frame 330, a first actuator 321, a second actuator 322 and a third actuator 323. The first, second and third actuators 321, 322, 323 are configured to move in relation to the frame 330 and configured to be operatively connected to the biopsy needle arrangement 20 in a similar manner as that described above in connection with FIGS. 1, 2 and 3a-d.

A triggering assembly 390 is connected at a proximal end of the body 31 of the actuator device 30. The triggering assembly 390 comprises trigger assembly parts, including a releaser 391 by which the proximal end of the first actuator 321 is held and whereby the sequence of the first, second and third actuators 321, 322, 323 being triggered to release their potential energy is initiated. Further details regarding a triggering assembly is outside the scope of the present disclosure.

The needle 21 is connected to the first actuator 321 via the needle connector 370. A biassing spring 369 provides a biassing force between the needle sheath 22 and the tip portion 23 of the needle 21 in the initial loaded configuration where the first, second and third actuators 321, 322, 323 have been loaded with potential energy as discussed above. As exemplified in FIG. 8a, the biassing spring 369 provides the biassing force by means of a pin arrangement having a guider 361 and a bias pin 364, the bias pin 364 arranged in a guide groove 362 of the first actuator 321 and connected to the needle connector 370 via a connector hole 365. When loading the first actuator 321 with potential energy via the spring 37, the biassing spring 369 will be compressed and provide a force that pulls the needle 21 in the proximal direction making the needle tip 23 abutting the distal end of the needle sheath 22, which is desirable as discussed above. Such an arrangement with a biassing spring 369 and bias pin 364 moving in the guide groove 362 also reduces the risk of damage to the needle tip 23 in case of "overloading" the spring 37 acting upon the first actuator 321 during the initial loading with potential energy as discussed above.

The needle sheath 22 is connected to the second actuator 322 by means of the sheath connector 350, which is configured to interact with the third actuator 323 via the groove 36 as discussed above. The third actuator 321 with its pin 34, pin base 341 and third spring 39 is configured to interact with the second pin guider 345 as discussed above wherein the pin 34 cooperates with the groove 342 and the groove 36 in the sheath connector 350. However, in the embodiments exemplified in FIGS. 8a and 8b, the pin guider 345 is arranged with its guiding groove 346 facing upwards and below, in the z direction, the needle arrangement 20 and attached in a hollow 340 to the frame base 331. The second slider 33 is configured with a guide space 378 in which the pin guider 345 is accommodated. The pin guider 345 is provided with resilience by means of a pin guider spring 349, in contrast to the embodiments discussed above where the pin guider 345 is attached to a leaf spring 348 that is fixed to, or being a part of, the housing 31.

The invention claimed is:

1. An actuator device for a biopsy needle arrangement, the actuator device comprising a frame, a first actuator, a second actuator and a third actuator, the first, second and third actuators being configured to move in relation to the frame and configured to be operatively connected to the biopsy needle arrangement, wherein:

the biopsy needle arrangement comprises a needle sheath and a needle, the needle sheath having proximal end and a distal end, the needle sheath including an elongated tube having a sheath opening at the distal end of the needle sheath, the needle having a proximal end and a distal end and a length that is greater than the length of the needle sheath, the needle comprising an elongated shaft portion configured to fit inside and slide relative to the needle sheath, and a tip portion connected to the shaft portion and located at the distal end of the needle, the tip portion having a transverse extension, or width, that is greater than a transverse extension, or width, of the sheath opening, the biopsy needle arrangement having a closed state and an open state, the tip portion abutting the needle sheath in the closed state, and the tip portion extending from the distal end of the needle sheath in the open state, the first actuator being configured to be operatively connected to the needle and configured to, with the needle arrangement in its closed state, push the needle distally in a sliding direction (x) relative to the needle sheath a first distance, d1, at which the needle arrangement is in its open state, the second actuator being configured to be operatively connected to the needle sheath and configured to, with the needle arrangement in its open state, push the needle sheath distally in the sliding direction (x) relative to the needle a second distance, d2, the third actuator being configured to be operatively connected to the needle sheath and configured to, with the needle arrangement in its open state, push the needle sheath distally in the sliding direction (x) relative to the needle a third distance, d3, where d3 is smaller than d2, at which the needle arrangement is in its closed state; and wherein the first actuator is configured to push the needle in motion having a first maximum velocity, v1, the second actuator is configured to push the needle sheath in motion having a second maximum velocity, v2, and the third actuator is configured to push the needle sheath in motion having a third maximum velocity, v3, where v3 is smaller than v2.

2. The actuator device of claim 1, wherein:

the first actuator comprises a first slider configured to slide relative to the frame in the sliding direction (x)

and a first spring, the first spring being configured to bias the first slider relative to the frame, the second actuator comprises a second slider configured to slide relative to the frame in the sliding direction (x) and a second spring, the second spring being configured to bias the second slider relative to the frame, and the third actuator comprises a pin and a third spring, the third spring being configured to bias the pin relative to the second slider.

3. The actuator device of claim 1, wherein:

the first, second, and third actuators are configured to bias the needle sheath with respect to the tip portion of the needle for all relative positions between the needle sheath and the tip portion.

4. The actuator device of claim 2, wherein:

the pin is configured to cooperate with a groove in a sheath connector attached to the needle sheath, the groove being aligned along at least a first transverse direction (y1) relative to the sliding direction (x) and wherein the pin is further configured to slide relative to the second actuator in a second transverse direction (y2) relative to the sliding direction (x), the second transverse direction (y2) being at an angle (a) to the first transverse direction (y1).

5. The actuator device of claim 1, wherein: the first actuator is configured to be releasably attached to the needle via a needle connector, the needle connector being configured to disengage the needle from the first actuator when the needle is subjected to a force in the sliding direction (x), which exceeds a threshold force.

6. The actuator device of claim 5, wherein:

the first actuator is configured to be attached to a first needle connector part of the needle connector; and wherein, when the needle disengages from the first actuator, the first needle connector part disengages from a second needle connector part attached to the needle and the second needle connector part moves distally in the sliding direction (x) relative to the first needle connector part.

7. The actuator device of claim 5, wherein:

the needle connector comprises a first needle connector part attached to the first actuator and a second needle connector part configured to be attached to the needle, and wherein:

when the needle disengages from the first actuator, the first needle connector part disengages from the second needle connector part and the second needle connector part moves distally in the sliding direction (x) relative to the first needle connector part.

8. The actuator device of claim 1, wherein:

the second actuator is configured to be releasably attached to the needle sheath via a sheath connector, the sheath connector being configured to disengage the needle sheath from the second actuator when the needle sheath is subjected to a force in a direction (−x) opposite the sliding direction (x), which exceeds a threshold force.

9. The actuator device of claim 8, wherein:

the second actuator is configured to be attached to a first sheath connector part of the sheath connector, and wherein:

when the needle sheath disengages from the second actuator, the first sheath connector part disengages from a second sheath connector part attached to the needle sheath and the first sheath connector part moves distally in the sliding direction (x) relative to the second sheath connector part.

10. The actuator device of claim 8, wherein:

the sheath connector comprises a first sheath connector part attached to the second actuator and a second sheath connector part configured to be attached to the needle sheath, and wherein:

when the needle sheath disengages from the second actuator, the first sheath connector part disengages from the second sheath connector part and the first sheath connector part moves distally in the sliding direction (x) relative to the second sheath connector part.

11. The actuator device of claim 6, wherein the needle connector is any of:

a click-fit configuration of the first and second connector parts, a break-apart configuration of the first and second connector parts, and a friction fit configuration of the first and second connector parts.

12. A biopsy system, comprising an actuator device and a biopsy needle arrangement, wherein the actuator device comprises a frame, a first actuator, a second actuator and a third actuator, the first, second and third actuators being configured to move in relation to the frame and configured to be operatively connected to the biopsy needle arrangement; wherein the biopsy needle arrangement comprises a needle sheath and a needle, the needle sheath having proximal end and a distal end, the needle sheath including an elongated tube having a sheath opening at the distal end of the needle sheath, the needle having a proximal end and a distal end and a length that is greater than the length of the needle sheath;

wherein the needle comprises an elongated shaft portion configured to fit inside and slide relative to the needle sheath, and a tip portion connected to the shaft portion and located at the distal end of the needle, the tip portion having a transverse extension, or width, that is greater than a transverse extension, or width, of the sheath opening;

wherein the biopsy needle arrangement has a closed state and an open state, the tip portion abutting the needle sheath in the closed state, and the tip portion extending from the distal end of the needle sheath in the open state;

wherein the first actuator is configured to be operatively connected to the needle and configured, with the needle arrangement in its closed state, to push the needle distally in a sliding direction (x) relative to the needle sheath a first distance, d1, at which the needle arrangement is in its open state;

wherein the second actuator is configured to be operatively connected to the needle sheath and configured, with the needle arrangement in its open state, to push the needle sheath distally in the sliding direction (x) relative to the needle a second distance d2;

wherein the third actuator is configured to be operatively connected to the needle sheath and configured, with the needle arrangement in its open state, to push the needle sheath distally in the sliding direction (x) relative to the needle a third distance d3, where d3 is smaller than d2, at which the needle arrangement is in its closed state; and wherein the first actuator is configured to be releasably attached to the needle via a needle connector, the needle connector being configured to disengage the needle from the first actuator when the needle is subjected to a force in the sliding direction (x), which exceeds a threshold force.

13. The biopsy system of claim 12, wherein the first actuator is configured to be attached to a first needle connector part of the needle connector; and wherein, when the needle disengages from the first actuator, the first needle connector part disengages from a second needle connector part attached to the needle and the second needle connector part moves distally in the sliding direction (x) relative to the first needle connector part.

14. The biopsy system of claim 12, wherein the needle connector comprises a first needle connector part attached to the first actuator and a second needle connector part configured to be attached to the needle; and wherein, when the needle disengages from the first actuator, the first needle connector part disengages from the second needle connector part and the second needle connector part moves distally in the sliding direction (x) relative to the first needle connector part.

15. The biopsy system of claim 13, wherein the needle connector is any of:

a click-fit configuration of the first and second connector parts;

a break-apart configuration of the first and second connector parts; and a friction fit configuration of the first and second connector parts.

16. A biopsy system, comprising an actuator device and a biopsy needle arrangement, wherein the actuator device comprises a frame, a first actuator, a second actuator and a third actuator, the first, second and third actuators being configured to move in relation to the frame and configured to be operatively connected to the biopsy needle arrangement; wherein the biopsy needle arrangement comprises a needle sheath and a needle, the needle sheath having proximal end and a distal end, the needle sheath including an elongated tube having a sheath opening at the distal end of the needle sheath, the needle having a proximal end and a distal end and a length that is greater than the length of the needle sheath;

wherein the needle comprises an elongated shaft portion configured to fit inside and slide relative to the needle sheath, and a tip portion connected to the shaft portion and located at the distal end of the needle, the tip portion having a transverse extension, or width, that is greater than a transverse extension, or width, of the sheath opening;

wherein the biopsy needle arrangement has a closed state and an open state, the tip portion abutting the needle sheath in the closed state, and the tip portion extending from the distal end of the needle sheath in the open state;

wherein the first actuator is configured to be operatively connected to the needle and configured, with the needle arrangement in its closed state, to push the needle distally in a sliding direction (x) relative to the needle sheath a first distance, d1, at which the needle arrangement is in its open state;

wherein the second actuator is configured to be operatively connected to the needle sheath and configured, with the needle arrangement in its open state, to push the needle sheath distally in the sliding direction (x) relative to the needle a second distance d2, wherein the third actuator is configured to be operatively connected to the needle sheath and configured, with the needle arrangement in its open state, to push the needle sheath distally in the sliding direction (x) relative to the needle a third distance d3, where d3 is smaller than d2, at which the needle arrangement is in its closed state; and wherein the second actuator is configured to be releasably attached to the needle sheath via a sheath connector, the sheath connector being configured to disengage the needle sheath from the second actuator when the needle sheath is subjected to a force in a direction (−x) opposite the sliding direction (x), which exceeds a threshold force.

17. The biopsy system of claim 16, wherein:

the second actuator is configured to be attached to a first sheath connector part of the sheath connector; and wherein, when the needle sheath disengages from the second actuator, the first sheath connector part disengages from a second sheath connector part attached to the needle sheath and the first sheath connector part moves distally in the sliding direction (x) relative to the second sheath connector part.

18. The biopsy system of claim 16, wherein:

the sheath connector comprises a first sheath connector part attached to the second actuator and a second sheath connector part configured to be attached to the needle sheath; and wherein, when the needle sheath disengages from the second actuator, the first sheath connector part disengages from the second sheath connector part and the first sheath connector part moves distally in the sliding direction (x) relative to the second sheath connector part.

19. The biopsy system of claim 17, wherein the needle connector is any of:

a click-fit configuration of the first and second connector parts;

a break-apart configuration of the first and second connector parts; and a friction fit configuration of the first and second connector parts.

* * * * *